(12) United States Patent
Pilvisto (10) Patent No.: US 6,699,182 B2
(45) Date of Patent: Mar. 2, 2004

(54) ENDOSCOPE-TYPE DEVICE, PARTICULARLY FOR EMERGENCY INTUBATION

(75) Inventor: Tönis Pilvisto, Tallinn (EE)

(73) Assignee: Xion GmbH, Berlin (DE)

( * ) Notice: Subject to any disclaimer, the term of this patent is extended or adjusted under 35 U.S.C. 154(b) by 0 days.

(21) Appl. No.: 10/041,709

(22) Filed: Jan. 8, 2002

(65) Prior Publication Data

US 2002/0177750 A1 Nov. 28, 2002

(30) Foreign Application Priority Data

Jan. 9, 2001 (DE) .......................................... 101 00 533

(51) Int. Cl.$^7$ .............................................. A61B 1/005
(52) U.S. Cl. ................... 600/146; 600/120; 128/200.26
(58) Field of Search .................. 600/139, 140, 600/146, 148, 150, 120, 194, 434; 604/95.04; 128/200.26

(56) References Cited

U.S. PATENT DOCUMENTS

| 3,557,780 A | * | 1/1971 | Sato ............................ 600/141 |
| 4,669,172 A | * | 6/1987 | Petruzzi ........................ 29/456 |
| 5,873,817 A | * | 2/1999 | Kokish et al. .............. 600/143 |

* cited by examiner

Primary Examiner—John Mulcahy
(74) Attorney, Agent, or Firm—Shaffer & Culbertson, L.L.P.

(57) ABSTRACT

The invention relates to an endoscope-type device, particularly an endoscope for emergency intubation, comprising a holding portion (7) and a shaft (1) which is configured to be flexible at least in partial areas, with at least two longitudinal bendable pulling and/or pushing elements acting on said shaft (1) in the axial direction at different distances from the proximal end, with said pulling and/or pushing elements extending as far as the proximal end and being lockably received in a fixing device, and with said endoscope-type device comprising an endoscope tip (50) whose movement is controllable via control means (54) and a control device (52) arranged in the proximal portion.

19 Claims, 5 Drawing Sheets

ENDOSCOPE-TYPE DEVICE, PARTICULARLY FOR EMERGENCY INTUBATION

TECHNICAL FIELD OF THE INVENTION

The invention relates to endoscope-type devices that may be manually formed and fixed in a particular shape prior to insertion into the area to be examined.

BACKGROUND OF THE INVENTION

Endoscope-type devices are used in many different fields of application, such as medicine, for example endoscopy, but also in engineering, for example as endoscope-type tools with an endoscope-type, flexible and formable shaft, and in general fields of application such as the controlled movement of extremities, particularly human extremities.

Intubation is the introduction of a tube (or a catheter) consisting of rubber or plastic material into the larynx and then into the trachea of the individual. It serves to maintain an effective exchange of gases, which is essential for providing organs with oxygen, among other things, and which is usually effected by respiration. In situations in which the patient is not capable of breathing himself as a result of an illness, an injury or medication, for example when a narcosis is carried out, artificial respiration has to be carried out. A prerequisite for this artificial respiration is a secure connection between the respirator and the patient's respiratory tract. In order to ensure that air is supplied to the respiratory organs only, without any air reaching the digestive tract via the esophagus, the tube is pushed with its distal end into the trachea via the mouth or the nose and is positioned there in such a way that both lobes of the lung are aerated. At the proximal end, the tube is connected with the tube system of the respirator via a standardized projection (connector).

If the tip of the tube is not positioned in the trachea, the lobes of the lung are not aerated. In this case, the blood flowing through the lung is not enriched with oxygen to a sufficient extent, and the organs are not provided with oxygen. Depending on how long the organs are not supplied with oxygen to a sufficient extent, apart from the complete restoration of all bodily functions, permanent cerebral injuries (such as a coma) or even death because of cardiac arrest might be possible. Faulty intubation, meaning those maneuvers of intubation in which the tube is not positioned correctly and the tip of the tube rests in the esophagus instead of the trachea, for example, will have the same consequences.

There are several methods and shapes of tubes to ensure secure positioning of the tip of the tube. With patients for whom no special anatomic or pathological conditions are to be taken into account, intubation is usually easy and fast to carry out with the usual methods, mainly the laryngoscopical intubation. However, difficulties may arise if there are pathological changes or anatomic peculiarities; in this case, the patient, who is not breathing, is subjected to artificial respiration by applying a combination of laryngoscopical intubation and fiber-optical intubation or by using devices employed specifically for this purpose.

In emergency intubation, which usually means the intubation of a person who has become unconscious and whose lung is liable to fill with water, it is necessary to supply air from outside as soon as possible in order to minimize the risk of lung injury.

In an emergency situation, that is, at the site of the accident and usually not in a hospital, this is done by means of laryngoscopical intubation; here, using a laryngoscope, lifting the tongue root and the epiglottis, the patient's pharynx is opened in order to gain a good view on the entrance to the larynx, the rima glottidis. If the rima glottidis is only partially visible, it is difficult to introduce the tube. One manages by changing the shape of the tube in its longitudinal axis until the tip of the tube can securely reach the entrance to the trachea. Prior to the present invention, changing the shape of the tube has been done by internally splinting the tube by means of a guide rod in the form of a flexible wire sheathed with plastic material which is inserted therein, which is so stable after bending that it transfers its shape in the longitudinal axis to the elastic tube. It is displaceable in the longitudinal axis within the tube, so it may also project from the distal tube end with its soft tip. Depending on the anatomic conditions, the guide rod is bent in such a way that its tip can be pushed through the rima glottidis and the tip of the tube can then be positioned in the trachea by sliding it over the guide rod. If the rima glottidis is not visible because of anatomic difficulties, so the path of the tube or the guide rod cannot be watched when it is pushed forward, there is a higher risk of injuries and a markedly reduced hitting accuracy. Although there are special instruments which are to make it possible to see the rima glottidis even under difficult conditions, the view through the tube is often obstructed when they are used because of the narrow conditions. For this reason, in difficult cases, the application of laryngoscopical intubation is not favorable.

Therefore, in these cases, fiber-optical intubation is preferably applied, in which an endoscope is used in order to find the entrance to the trachea and to illuminate and make visible the area to be inspected. Furthermore, by means of a mechanism mounted on the holding portion of the endoscope, the position of the tip of the endoscope can be changed, and it can therefore be visibly pushed through the rima glottidis. The tube previously placed upon the tube of the endoscope is then pushed forward as far as into the trachea; then, the endoscope is pulled out of the tube which has been positioned correctly, and the tube is fixed to the patient's head and is connected with the respirator.

However, the fiber-optical method cannot be carried out optimally in all cases, either. It is particularly difficult if the patient is lying on his back and his musculature is slackened, because the tongue root falls back, thus blocking the path to the trachea. Furthermore, as one hand is required to guide the endoscope—usually by means of the surrounding tube—in fiber-optical intubation and a second hand is required to operate the mechanism of the endoscope, another person is necessary to lift the tongue root by means of a laryngoscope; however, such a person is not necessarily present in case of an emergency.

In the document EP 0 742 026 A, a flexible and simultaneously formable endoscope with a viewing lens was therefore suggested, over which a tube can be slid. Here, formability and flexibility was to be obtained by an articulated rod whose individual adjacent links with convex or concave surfaces could be tensed by tensional or compressive forces. What was disadvantageous, however, was that tests during manufacturing revealed that this principle is very complex because of the frictional forces which are difficult to control and that sufficient flexibility with simultaneously adjustable stiffness cannot be realized with this endoscope.

SUMMARY OF THE INVENTION

It is an object of the present invention to provide an endoscope-type device at low cost and in a simple manner, which overcomes the above-mentioned drawbacks and which includes a formable and stiff shaft which, after releasing, changes into a flexible condition at least in partial areas.

According to the invention by arranging longitudinal bendable pulling and/or pushing elements or their distal ends at the shaft at different distances from the proximal end, the shaft can manually be brought into a desired shape in the flexible, that is, non-fixed condition, which becomes stiff by locking the pulling and/or pushing elements. Here, the pulling and/or pushing elements, which are limited at least in the pushing or pulling direction, act on the shaft, and the stability of the stiffness can be increased by a bilateral limitation. In spite of the fact that a pre-formed shape of the shaft has been locked, the introduction is made easier by the controllable tip of the endoscope, particularly in extreme situations or for physicians with less experience, because when introducing the device into the trachea—for example in case of an emergency intubation—the respective next section of the path ahead can be watched via the lens and the tip can be adjusted to the respective curves. As a result, for example even in case of rupture of the trachea, it is possible to compensate the existing displacement of the trachea ends (which might be several millimeters) at the point of rupture by moving the tip correspondingly and to guarantee an easy and fast introduction of a tube or a trachea catheter (slid over the shaft), even past such an extreme position.

In an advantageous embodiment of the invention, the tip of the device is controllable in only one plane to be moved up and down or to the left and to the right; advantageously, this movement can already be achieved with a small number of control means and the cross-section of the shaft within which the control means are housed can be maintained correspondingly small.

By rotating the entire device about its longitudinal axis, however, arbitrary directions or head positions can be reached, with such a rotation being possible in a specific range without causing an injury to the trachea even in case of emergency intubation. Of course, with corresponding dimensions, it is also conceivable to arrange further control means in the shaft up to the tip so that it is made possible to control the tip of the device in all directions, as is the case with conventional flexible endoscopes. As, in the preferred embodiment of the invention, the movability and formability may be limited to a movement within the same plane including the longitudinal axis of the device, too (for example, an S-shaped movement), as is the case with the controllability of the tip, the rigidity in other planes and thus the resistance to upsetting deformation or distortion is particularly high, especially in case of a rotation about the longitudinal axis of the device. In this case, the entire device constitutes a body which is naturally rigid or strong, thus resisting movements in other directions.

In an embodiment of the invention, the pulling and/or pushing elements, for example steel strands, may be movably received in guide elements at the shaft in the longitudinal direction. Hereby, the stability of the rigidity is advantageously increased, as the path length of the pulling and/or pushing elements is defined exactly by the fact that the guide elements receiving the pulling and/or pushing elements are fixedly positioned.

In a further embodiment of the invention, seen from a cross-sectional view, the pulling and/or pushing elements are positioned in a ring-shaped arrangement within said shaft (1) at the inner periphery thereof, so their lever action and thus the stability of the rigidity, which increases with increasing distance from the center line, is advantageously improved.

In a further embodiment of the invention, lateral guide means are arranged inside the shaft which, seen in a cross-sectional view, are opposed to each other, and which are fixedly connected with the shaft at least in partial areas. Advantageously, this will prevent undesired bending of the shaft within the plane defined by lateral guide means.

In a further embodiment of the invention, the channel is configured as a channel for an optical light guide and an optical image guide or as a channel for instruments. Advantageously, this makes it possible to check and facilitate the arrival at an aiming point when the endoscope-type device is introduced into a non-visible portion.

In a further embodiment of the invention, pulling and/or pushing elements act on the shaft in pairs in the axial direction, substantially at equal distances from the proximal end. Hereby, as a result of the cooperation of pulling and pushing forces of a pair, stability may be increased. Such pairs of pulling and/or pushing elements may be arranged point-symmetrically at the shaft in order to advantageously exert the optimum stability in a freely movable shaft without any lateral limitation with their maximum distance from each other.

In case of lateral limitation to the movement, however, it may also be advantageous for an optimum effect of the forces to arrange pairs of pulling and/or pushing elements at the shaft to be symmetrical to the horizontal or the vertical axis, in other words: symmetrical to the plane defined by the lateral guide means, respectively.

DESCRIPTION OF PREFERRED EMBODIMENTS

FIGS. 1 to 5 show a first embodiment of the invention, which corresponds to the endoscope-type device of German patent application 199 32 022.5, which has not been published yet.

Figure 1:
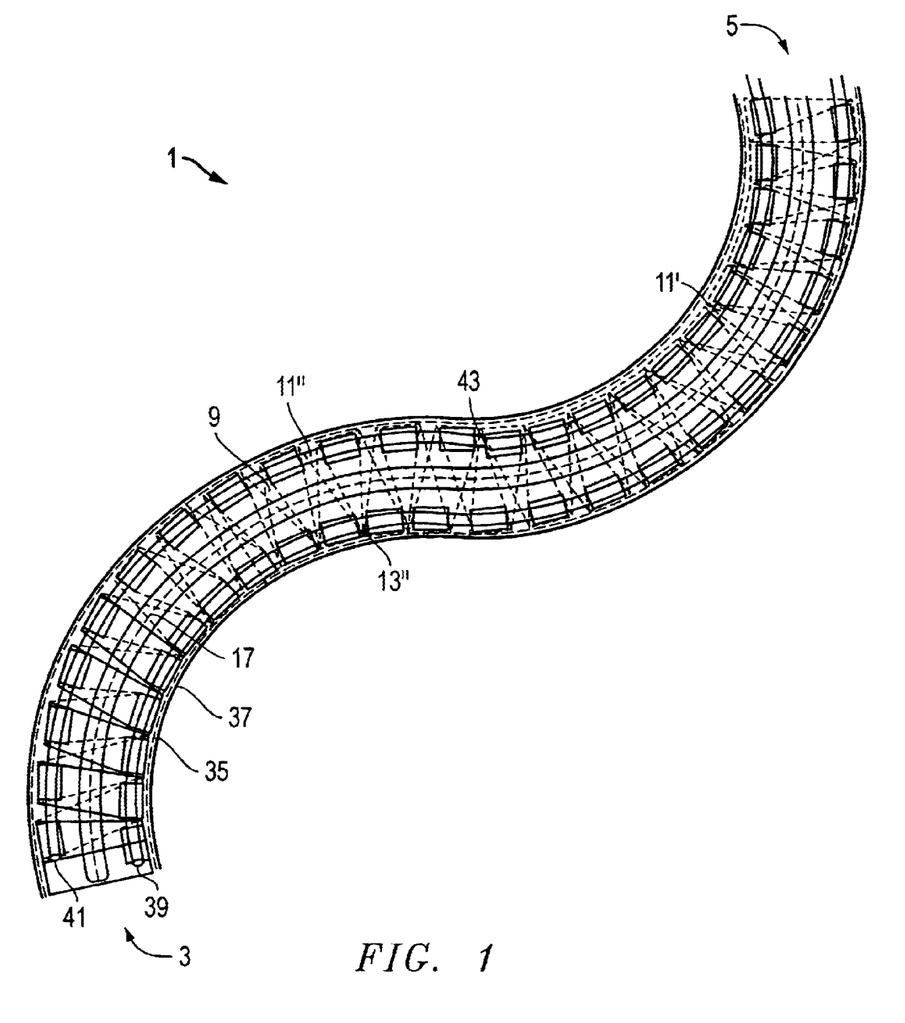
FIG. 1 shows a longitudinal sectional view of a shaft of an endoscope-type device according to the invention.
Figure 4:
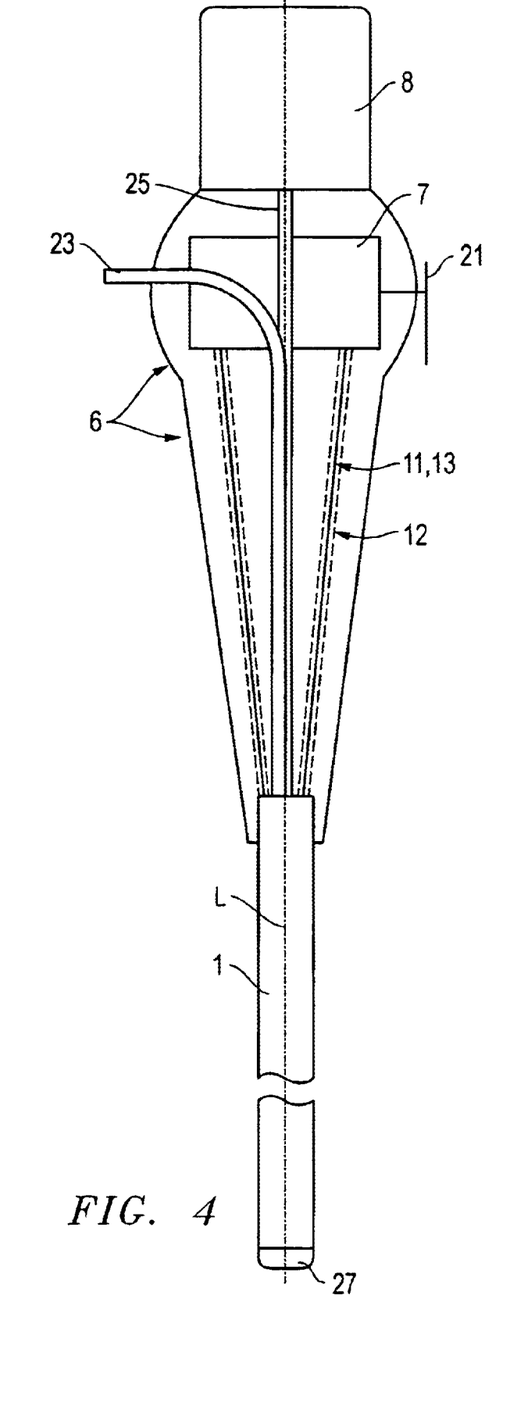
FIG. 4 shows a lateral view in partial section of the endoscope-type device according to the invention.

FIG. 1 shows a shaft 1 of an endoscope-type device according to the invention with a distal end 3 and a proximal end 5. Adjacent the proximal end 5 of the shaft 1, a housing 6 with a holding portion 7 (see FIG. 4) and an eyepiece 8 as shown in FIG. 4 is arranged.

Figure 3:
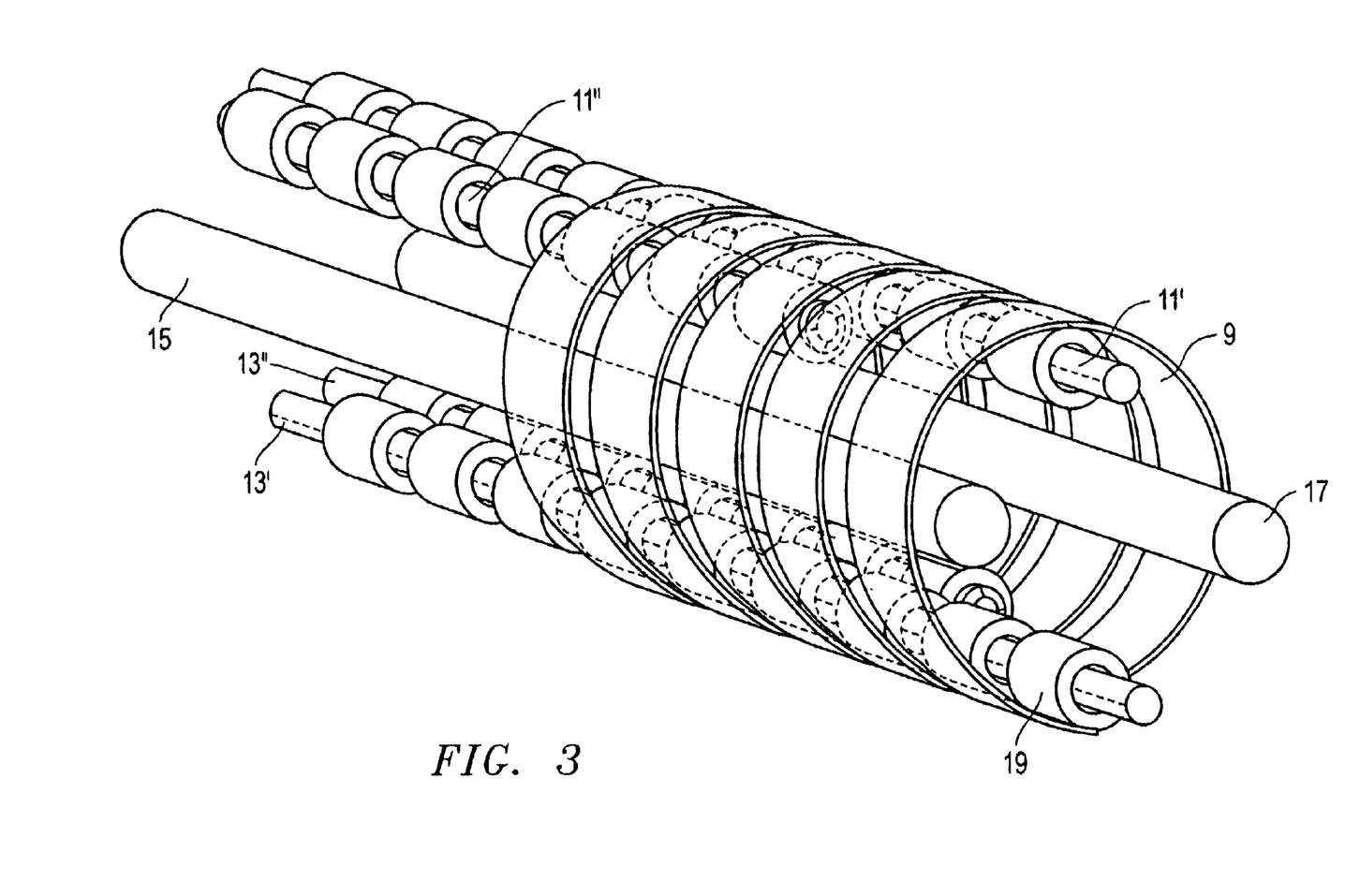
FIG. 3 shows a perspective, schematic view of the structure of a partial portion of the shaft according to FIG. 1.

As will be apparent from FIG. 3, the shaft 1 consists of a spring with a ring-shaped cross-section, particularly a leaf spring 9, which extends from the proximal end 5 to the distal end 3 of the shaft 1. The spring, the ring-shaped cross-section of which includes both the circular shape, the oval shape and the polygonal shape, is made of steel or plastic material, for example.

At the inner periphery or the inner wall of the leaf spring 9, several—for example five—ropes 11 to 11"" guided on top and five ropes 13 to 13"" guided at the bottom and lateral guide means at the left side 15 and the right side 17 are arranged.

Figure 2:
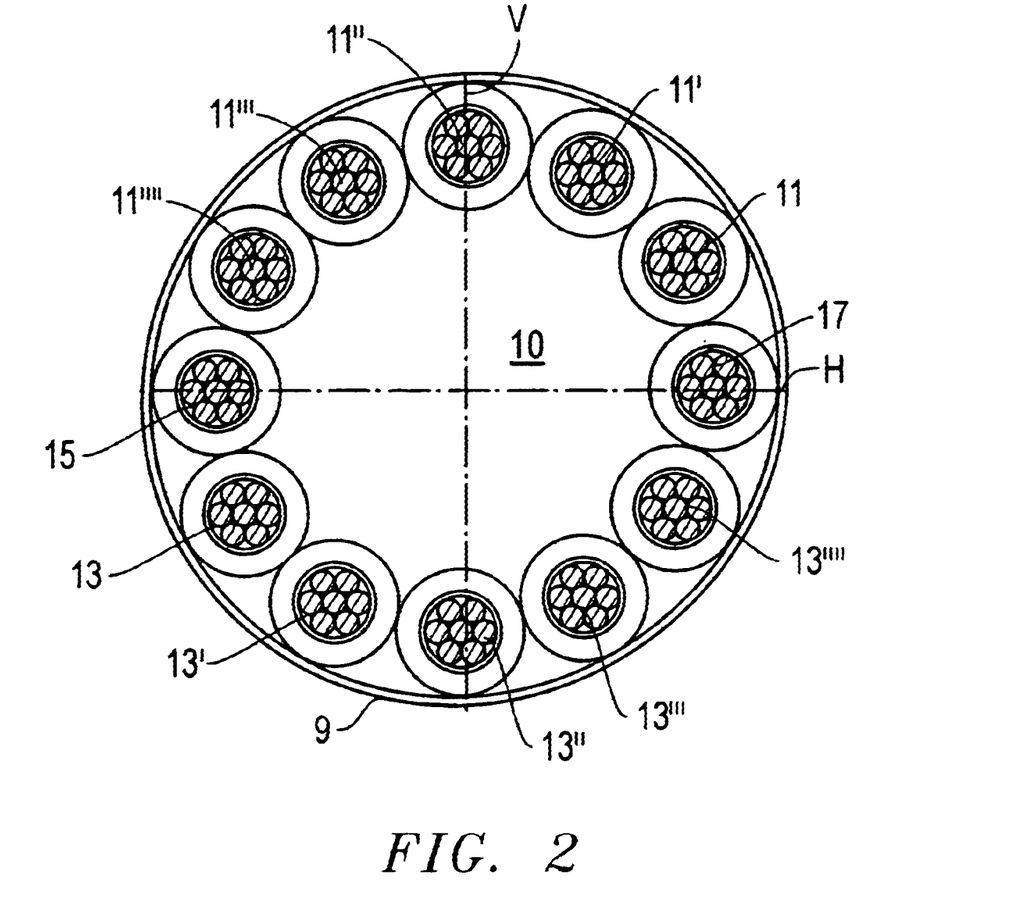
FIG. 2 shows a cross-sectional view of the shaft according to FIG. 1.

The cross-sectional distribution of ropes 11 to 11"", 13 to 13"", 15 and 17 shown in FIG. 2 illustrates that the lateral guide means are positioned, when seen from a cross-sectional view, at the inner periphery of the leaf spring 9 in such a way that they lie opposite to each other in a horizontal mid-plane or are arranged on a horizontal center line H. Above and below the axis H, ropes 11 to 11"" and 13 to 13"" guided on top and at the bottom are arranged at the inner periphery, particularly at equal distances.

As will be apparent from FIG. 2, all ropes may be configured as strands, particularly made of steel or plastic material, with five leads, for example. The ropes 11 to 11"" and 13 to 13"" guided on top and at the bottom extend in guide elements 19 which may be configured to be ring-shaped and which are arranged at the inner periphery in the longitudinal direction and along a longitudinal axis in distances, particularly equal distances, corresponding to the turn or the convolution and the width of the leaf spring, for example by laser welding.

The ropes 11 to 11"" and 13 to 13"", whose outer periphery is of somewhat smaller dimension than the inner periphery of the guide elements 19, are guided out of the proximal end 5 of the shaft in a first conically widened portion of the housing 6 shown in FIG. 4 and extend as far as into the holding portion 7 arranged in the adjacent widened and conical portion. The diameter of the—seen from a cross-sectional view—ring-shaped arrangement of the guided ropes 11 to 11"" and 13 to 13"" increases from some millimeters, such as 3 mm in the area of the shaft (provided that the shaft 1 has an outer diameter of approximately 5 to 6 mm) to approximately the double value. In this area, the ropes 11 to 11"" and 13 to 13"" may extend within guide means, too—such as rigid guide means 12 shown in dotted lines in the drawing—in spite of the fact that the holding portion 7 is fixedly arranged in the housing 6, so as not to exert pulling forces only, but also pushing forces.

In its first portion adjacent the proximal end 5 of the shaft 1, the housing 6 is widened correspondingly and is configured to be conical, for example. Next to this first portion, the housing 6 continues to form a widened spherical portion with the holding portion 7. In the first portion, the guided ropes 11 to 11"" and 13 to 13"" are guided in a rigid sleeve which is fixedly arranged in the housing.

In this holding portion 7, a fixing mechanism is located which is not shown in greater detail in the drawings and which can be operated by an operating element, such as an operating lever 21, in order to release the proximal ends of the ropes 11 and 13 so as to be movable in their longitudinal direction or to fix them. A fixing device of this kind may be configured as a guide plate arranged perpendicularly to the plane of the drawings, which contains holes with the corresponding geometry, e.g. circular, in one line or in two parallel rows in order to receive the ropes 11 to 13 so as to be movable in the longitudinal direction. Of course, the holes in the guide plate have a slightly larger inner diameter than the outer diameter of the ropes 11 to 11"" and 13 to 13"". In order to block or release the ropes in their longitudinal direction, a second guide plate which is configured to correspond to the first guide plate and is arranged adjacent to it, and whose holes are aligned in the releasing position, can be displaced with respect to the first plate via the operating lever 21, for example. In this case, the rope ends are clamped in their respective longitudinal position. Thus, the operating lever 21 and the second guide plate, which acts as a clamping plate and can be displaced with respect to the first plate parallel thereto, provide a releasing and a locking position; in these positions, the operating lever and thus the clamping plate can be fixed via locking means or can be pre-stressed permanently in a position, particularly the fixing position, by means of a spring, for example, so as to be put into the releasing position only during the operation of the operating lever. At least in the portion in which they are capable of being displaced in the longitudinal direction inside the fixing device, the rope ends may be configured as rods or may be surrounded by rigid sleeves. Advantageously, this contributes to prevent deterioration or wear, such as splicing of the ends as a result of continued use.

As will be apparent from FIG. 4, in the area of the partially spherical section which is located adjacent the conical first section of the housing and which includes the holding element 7, an optical light guide is guided from inside the housing to the outside so as to be connected to a light source which is not shown in the drawings. The cylindrical portion, which forms the proximal end of the housing and which has a smaller diameter than the spherical section, is configured as an eyepiece 8 (not shown in greater detail) for the operating personnel, such as the physician. This eyepiece 8 is connected with an optical image guide 25 which, like the optical light guide 23, extends inside the endoscope to the distal end thereof.

At the distal end 3 of the endoscope or the shaft 1, there is an endoscope head 27, which is sealed off from the ambience like the entire shaft 1.

Figure 5:
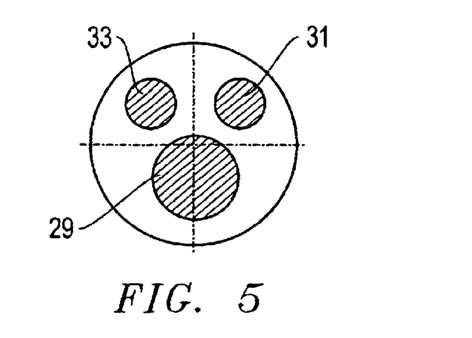
FIG. 5 shows a front view of the endoscope head shown in FIG. 4.

As will be apparent from FIG. 5, the endoscope head includes an image lens 29 which is connected with the optical image guide 25 inside the shaft, and two light lenses 31 and 33, which are connected with the optical light guide via a Y-connection in the interior of the shaft, which comprises a free space 10 (see FIG. 2) in the form of a channel, for example, in a manner which is not shown in greater detail.

As shown in FIG. 1, for reasons of stability, the leaf spring 9 is surrounded by an elastic net 35, which consists of steel braiding, for example, and which is sheathed by a flexible sleeve 37 made of plastic material or rubber. This sleeve 37 seals off the shaft 1 and, as the case may be, also the head 27 from the ambience and, advantageously, reduces friction inside a tube or catheter at the same time.

As will be apparent from FIG. 1, the ropes 11 to 11"" and 13 to 13"" guided in guide elements along an axis parallel to the longitudinal axis L terminate at their ends opposite to the proximal end at different distances from the proximal end. Their end points are fixedly connected with the corresponding guide elements, for example by laser welding, or they have a larger head which projects from the corresponding guide element in the distal direction and serves as a stop means to this guide element in the proximal direction.

For reasons of clarity, only the ropes 11', 11" and 13" as well as their ends 43, 41 and 39 are illustrated in FIG. 4. In the preferred embodiment shown in the drawing, the ropes are subdivided in pairs of approximately the same rope length, point-symmetrically or symmetrically with the axis H, for example; the pairs of ropes,(such as 11; 13, 11 '; 13', 11"; 13", 11"'; 13' and 11""; 13"") are fixed to the shaft 1 or the leaf spring 9 at different distances from the proximal end 5 or form a stop means in the direction towards the proximal end 5, i.e. in the pulling direction of the ropes.

The different fixing points may subdivide the shaft into sections of equal length; in the area which is likely to be subjected to strong bending forces by specific forms of use of the device, the distances may advantageously be chosen to be smaller in order to define the bending action more exactly. Contrasting to this, in parts which are likely to remain straight or parts in which no specific exact bending is desired, the distances may be made larger. As is apparent from FIG. 1, after clamping or fixing the rope ends, stiffening of the last shape chosen in the flexible condition will occur in the direction of fixing. Here, the rope lengths of ropes 11 to 11"" and 13 to 13"" are fixed, and thus also the distances of the fixing points, i.e. the respective rope ends 39, 41, 43 etc., from the distal end. Of course, the number of ropes and of fixing points may be increased in order to keep the possible extension or elongation between longitudinally adjacent fixing points within small tolerances. Furthermore, in the arrangement in pairs, stability is supported not only by the pulling force, but also by the pushing, force of the respective partner of a traction rope. Moreover, the leaf spring 9, too, has ascertain tendency to subdivide the entire distance between two adjacent fixing points in the longitudinal direction into equal distances of adjacent turns or adjacent guide elements 19 in the longitudinal direction in this area, if possible.

As, in the embodiment illustrated, the endoscope-type device is to be used for emergency intubation, an S-shape is to be obtained for anatomic reasons, for example, which has to be given to a flexible tube or catheter which has previously been placed onto the shaft.

This S-shape is to be formed in one plane so that lateral forces can be exerted when introducing the device, too. To achieve this, in the embodiment, the lateral guide means 15 and 17 are not only connected to the shaft 1 or the leaf spring 9 at their end points—contrasting to the guided ropes 11 to 11"" and 13 to 13""—, but at several, advantageously all points at which they contact the leaf spring 9 along the longitudinal axis thereof. In this way, the opposite sides are neither extendable nor compressible along these axes in their length, so bending of the shaft 1 in the plane of the two lateral guide means 15 and 17, i.e. in a plane perpendicular to the plane of the drawing FIG. 1, is avoided.

After the pharynx has been opened with one:hand using a laryngoscope, the shaft 1 with the tube is introduced into the lung via the trachea with the other hand.

If the previously formed S-shape should prove to be not ideal when introducing the device, it is possible to change the stable shape by releasing the fixing device using the operating lever 21 so that the portion which has already partially been introduced adjusts to the different S-shape. In this shape which has been adjusted to the anatomic conditions of the individual case, the device can be further introduced until the physician detects via the eyepiece 8 that the entrance to the lung has been reached. Then, the rigid S-form of the endoscope is changed by releasing the fixing device so that the endoscope, which is now flexible, or the shaft 1 thereof can be pulled out of the tube. There are no or only very small frictional forces between the flexible tube and the shaft 1 so that inadvertent extraction of the tube is avoided.

Figure 6:
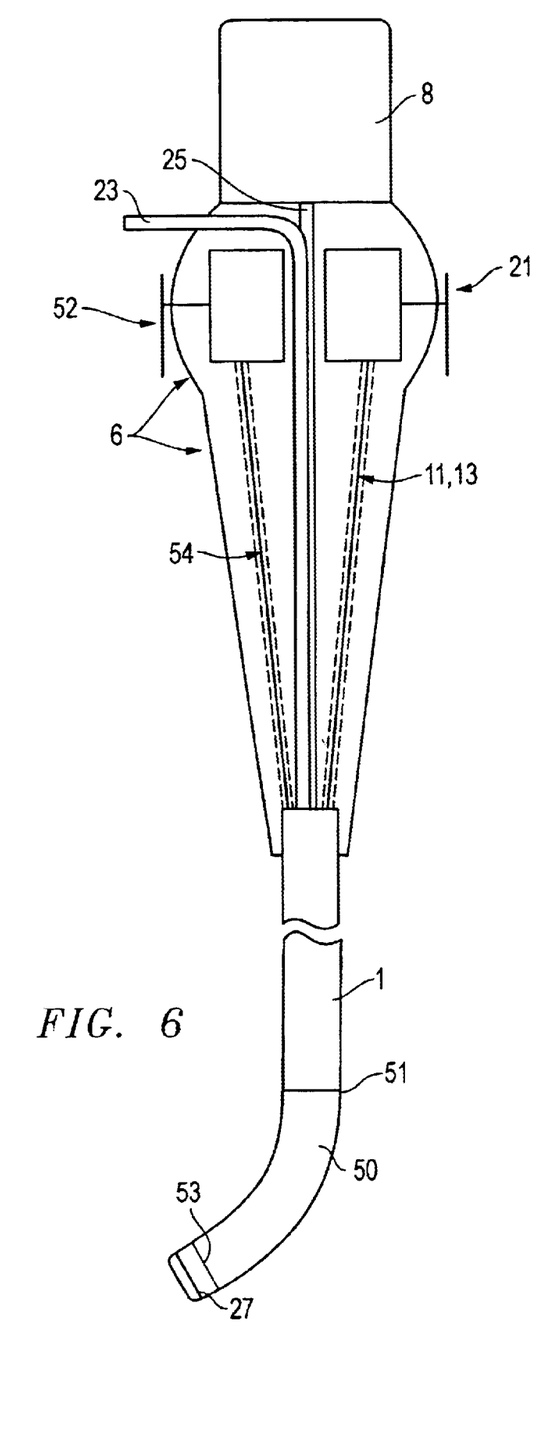
FIG. 6 shows a lateral view in partial section of another embodiment of an endoscope-type device according to the invention.
Figure 7:
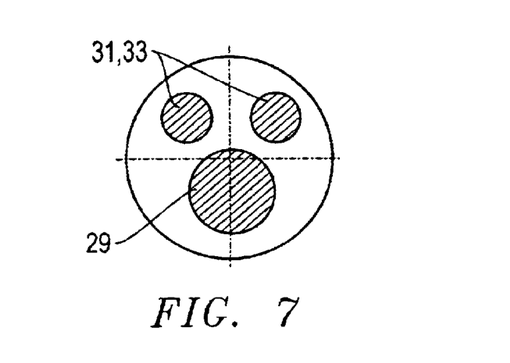
FIG. 7 shows a front view of the endoscope head shown in FIG. 6.

FIGS. 6 and 7 show another embodiment of an endoscope-type device according to the invention, which—contrasting to the embodiment explained above—comprises a controllable tip 50. This controllable tip 50, which is shown in its bent position (bent to the left) in FIG. 6, extends from the dividing line 51 to the dividing line 53, so the shaft 1 of the endoscope does not directly merge into the endoscope head 27 like in the embodiment explained above, but there is the controllable endoscope tip 50 between the end of the shaft 1 (dividing line 51) and the beginning of the endoscope head 27 (dividing line 53). This tip is substantially shorter in its longitudinal dimension in relation to the length of the shaft 1 of the endoscope; this relation may be approximately 1:10, for example, with a tip length of 2 to 4 cm, particularly 3 cm, and a shaft length of 30 to 40 cm, for example.

The length of the shaft corresponds to the length of a commonly used tube, for example a trachea catheter, which is to be used in an emergency intubation. Advantageously, the tip 50 may project from the catheter which has been placed upon the shaft 1, as the catheter is relatively rigid in such a short portion (2 to 4 cm) and would impede a movement of the endoscope tip 50 to a considerable extent or would even make it impossible. The movement of the endoscope tip 50 via control means which are configured as traction wires 54 of a Bowden wire device, for example, and which are only shown schematically in the drawings, is effected via a control device arranged in the proximal portion, which may be configured as a control lever 52; this control or the movability of the endoscope tip 50 may be effected by conventional mechanisms of the type used for controlling the shaft of flexible endoscopes.

As for the rest, this further embodiment is configured like the embodiment explained above, apart from the controllable tip and from the means 52, 54 to control it, so this embodiment has all the advantages of the aforesaid embodiment and is additionally controllable in the small tip portion because of the configuration of a controllable tip 50. Advantageously, in extreme cases such as a strongly bent trachea or a trachea with a rupture, a person handling the device, usually the emergency physician, can therefore make control movements at the tip when introducing a catheter placed upon the shaft 1, so introducing the catheter is made easier.

This makes it possible in case of a torn trachea, for example, which is displaced by several millimeters—5 to 10 mm, for example—at the point of rupture, to compensate this displacement when introducing the endoscope or during intubation by;correspondingly moving the endoscope tip 50 via the lever 52 and then easily and quickly introducing the tip and thus the catheter placed upon the shaft 1 into the displaced portion of the trachea.

However, this flexible controllable tip 50 also makes it considerably easier for less experienced physicians to introduce an air catheter, particularly when treating patients in an emergency situation, because during the introduction, the path taken inside the potentially injured trachea can be watched at any time via the eyepiece, and the tip 50 can be adjusted to unexpected or extreme situations accordingly. Because of the small dimensions of the flexible controllable tip 50, which of course cannot be fixed—as is the case with conventional flexible endoscope shafts—and thus be brought into a rigid condition (to act against forces and pressures occurring when introducing the device) like the shaft 1, the advantages of a fixable rigid shaft 1 explained above for the first embodiment are maintained, namely, manual bending of the shaft 1 into a corresponding shape (by a person handling the device, particularly an emergency-physician), fixing the shaft in this shape so that no upsetting deformation (and, as the case may be, damage to the device, for example, the lens) of the shaft 1 may occur during the introduction thereof, and changing this rigid condition again in order to pull the endoscope out of the catheter introduced as easily as possible and with minimum friction, or changing this condition during the introduction (thus making it possible to adjust the device to the existing shape of the trachea) and fixing the shaft 1 again in this adjusted condition, in order to make it possible to exert further pressure or force substantially in the longitudinal direction, i.e. the direction of introduction of the endoscope with the catheter without the danger of any upsetting deformation of the shaft 1.

In the preferred embodiment, the endoscope tip 50 is pivotable in one plane only, such as in the plane of the drawing, as shown, to be pivotable upwards and downwards or to the left and to the right; advantageously, this movement can already be achieved with a small number of control ropes 54 and the cross-section of the shaft 1 and the tip 50 can be kept correspondingly small. By turning the entire device about its longitudinal axis, however, arbitrary directions can be reached, with such turning being even possible within a certain range without causing damage to the trachea when the device is used in emergency intubation. Of course, it is also conceivable to arrange additional control ropes 54 in the shaft 1 of the endoscope up to the tip 50—provided that the device has corresponding dimensions—so that controllability of the endoscope tip 50 in all directions like in conventional flexible endoscopes is made possible. As, in the preferred embodiment of the invention, the capability of the shaft 1 to be formed can be limited to a movement within the same plane (such as an S-shaped movement) like the controllability of the tip 50, the rigidity in other planes and thus the resistance to upsetting deformation or distortion, particularly if the device is rotated about its longitudinal axis, is particularly high.

The invention is not limited to endoscopy, particularly emergency intubation, but may be applied to all endoscope-type devices. It is pointed out explicitly that this term is to be interpreted broadly according to the invention; for example, bendable shafts in technology relating to tools, particularly for extending screw drivers, drills and the like, and bendable links which are configured to be flexible or bendable at least in partial portions and in which stiffening to an arbitrary predetermined shape is desired, are to be included in this definition. Advantageously, the formability and flexibility described above may exist along the entire shaft 1. The rigidity in the fixed position makes it possible to obtain a pre-formable structure which is subsequently resistant to pressures and forces which occur when the device is introduced into a trachea, for example, so that a potentially resulting upsetting deformation can be avoided. Contrasting to flexible endoscopes with a controllable shaft, such as a bronchoscope, the rigid shape is maintained once it has been taken (until the fixing device is released) so that damage by upsetting deformation, such as damage to the lens, and expensive repairing can be avoided.

What is claimed is:

1. A device including:
   (a) a shaft having at least one flexible portion along its length between a proximal end and a distal end;
   (b) at least two longitudinally bendable pulling and/or pushing elements acting on the shaft in an axial direction of the shaft at different distances from the proximal end of the shaft, the at least two pulling and/or pushing elements each extending to the proximal end of the shaft;
   (c) a fixing device located in a fixed position with respect to the shaft adjacent to the proximal end of the shaft, the fixing device having each of the at least two pulling and/or pushing elements extending there through, and being adapted to reside alternatively in a releasing position in which the pulling and/or pushing elements are unsecured to the fixing device and are substantially free to move axially there through, or a locking position in which each pulling and/or pushing element is fixed in place with respect to the fixing device;
   (d) an elongated tip having a proximal end connected to the distal end of the shaft and a distal end extending from the shaft; and
   (e) a tip control device located adjacent to the proximal end of the shaft and connected to the elongated tip for controlling the longitudinal form of the elongated tip.

2. The device of claim 1 wherein the shaft comprises a leaf spring having a ring-shaped cross-section.

3. The device of claim 1 wherein each pulling and/or pushing element comprises a rope which is substantially rigid in its longitudinal direction.

4. The device of claim 1 wherein each pulling and/or pushing element is received within a respective guide element within the shaft so as to be slidable longitudinally with respect to the respective guide element.

5. The device of claim 1 including at least four pulling and/or pushing elements and wherein the pulling and/or pushing elements are arranged in a ring shape about an inner periphery of the shaft.

6. The device of claim 1 wherein each pulling and/or pushing element acts upon the shaft in such a way that it is limited to pulling and pushing directions for the respective pulling and/or pushing element.

7. The device of claim 1 further including two lateral guides extending longitudinally inside the s on opposite sides thereof, each lateral guide being fixed to the shaft along at least a portion of the length of the respective lateral guide.

8. The device of claim 1 wherein the shaft includes an interior longitudinal channel.

9. The device of claim 8 further including an optical light guide or an optical image guide extending within the channel.

10. The device of claim 1 wherein the pulling and/or pushing elements are arranged in pairs with each pulling and/or pushing element in a respective pair engaging the shaft in the axial direction at substantially the same distance from the proximal end of the shaft.

11. The device of claim 1 wherein the form of the elongated tip is limited to bends in a single plane.

12. A device including:
   (a) a shaft having at least one flexible portion along its length between a proximal end and a distal end;
   (b) a housing connected to the proximal end of the shaft;
   (c) at least two longitudinally bendable pulling and/or pushing elements acting on the shaft in an axial direction of the shaft at different distances from the proximal end of the shaft, the at least two pulling and/or pushing elements each extending to the housing;
   (d) a fixing device located in the housing, the fixing device having each of the at least two pulling and/or pushing elements extending there through, and big adapted to reside alternatively in a releasing position in which the pulling and/or pushing elements are unsecured to the fixing device and substantially free to move axially there through, or a locking position in which each pulling and/or pushing element is fixed in place with respect to the fixing device,
   (e) an elongated tip having a proximal end connected to the distal end of the shaft and a distal end extending from the shaft, the elongated tip having a form that is controllable via controls associated with the housing.

13. The device of claim 12 wherein the shaft comprises a leaf spring having a ring-shaped cross-section.

14. The device of claim 12 wherein each pulling and/or pushing element is received a respective guide element within the shaft so as to be slidable longitudinally with respect to the respective guide element.

15. The device of claim 12 further including two lateral guides extending longitudinally inside the shaft on opposite sides thereof, each lateral guide being fixed to the shaft along at least a portion of the length of the respective lateral guide so as to limit the form of the shaft to forms lying in a single plane.

16. The device of claim 12 wherein the shaft includes an interior longitudinal channel.

17. The device of claim 16 further including an optical light guide or an optical image guide extending within the channel.

18. The device of claim 12 wherein the pulling and/or pushing elements are arranged in pairs with each pulling and/or pushing element in a respective pair engaging the shaft in the axial direction at substantially the same distance from the proximal end of the shaft.

19. The device of claim 12 wherein the form of the elongated tip is limited to bends in a single plane.

* * * * *

UNITED STATES PATENT AND TRADEMARK OFFICE
CERTIFICATE OF CORRECTION

PATENT NO. : 6,699,182 B2
DATED : March 2, 2004
INVENTOR(S) : Tönis Pilvisto

It is certified that error appears in the above-identified patent and that said Letters Patent is hereby corrected as shown below:

Column 6,
Line 64, change "13'" to -- 13"" --.

Column 7,
Line 19, change "pushing," to -- pushing --.
Line 21, change "ascertain" to -- a certain --.
Line 43, change "one:hand" to -- one hand --.

Column 8,
Line 43, change "by;correspondingly" to -- by correspondingly --.

Column 10,
Line 31, change "s" to -- shaft --.
Line 58, change "big" to -- being --.
Line 64, change "device," to -- device; --.

Column 11,
Line 6, change, "received a" to -- received within a --

Signed and Sealed this

Fifteenth Day of June, 2004

JON W. DUDAS
*Acting Director of the United States Patent and Trademark Office*